United States Patent [19]

Rambosek

[11] 4,002,167

[45] Jan. 11, 1977

[54] ANIMAL GAS MASK ASSEMBLY

[75] Inventor: George Phillip Rambosek, St. Paul, Minn.

[73] Assignee: Minnesota Mining and Manufacturing Company, St. Paul, Minn.

[22] Filed: Feb. 20, 1976

[21] Appl. No.: 659,840

Related U.S. Application Data

[63] Continuation-in-part of Ser. No. 505,618, Sept. 13, 1974, abandoned.

[52] U.S. Cl. .............................. 128/205; 128/146; 128/146.7
[51] Int. Cl.² ...................................... A61M 16/00
[58] Field of Search .......... 128/185, 186, 187, 188, 128/191 R, 192, 193, 194, 195, 196, 203, 205, 206, 212, 140 R, 141 R, 142 R, 142.6, 146, 146.2, 146.5, 146.6, 146.7; 119/129

[56] References Cited

UNITED STATES PATENTS

| 530,321 | 12/1894 | Boesger et al. | 128/195 |
| 2,312,714 | 3/1943 | Herbin | 128/142.6 |
| 2,843,119 | 7/1958 | Glasser | 128/194 |
| 3,491,755 | 1/1970 | Barghini et al. | 128/146.6 |

FOREIGN PATENTS OR APPLICATIONS

| 19,018 | 1895 | United Kingdom | 128/195 |

Primary Examiner—Robert W. Michell
Assistant Examiner—Henry J. Recla
Attorney, Agent, or Firm—Alexander, Sell, Steldt & DeLaHunt

[57] ABSTRACT

A gas mask assembly for snouted animals is disclosed having a nose cap member for covering the nostrils and anterior portion of the animal's snout and having an opening therein for the attachment of a breathing tube. An abutment in the nose cap member prevents the animal's nostrils from becoming occluded by said nose cap member. A flexible sleeve member, formed from substantially gas impermeable material, is secured to the nose cap, and an immobilizing cinch is secured to the marginal portion of the sleeve member to afford sealing engagement for the sleeve member against the animal's snout and to restrain the animal's movements.

4 Claims, 7 Drawing Figures

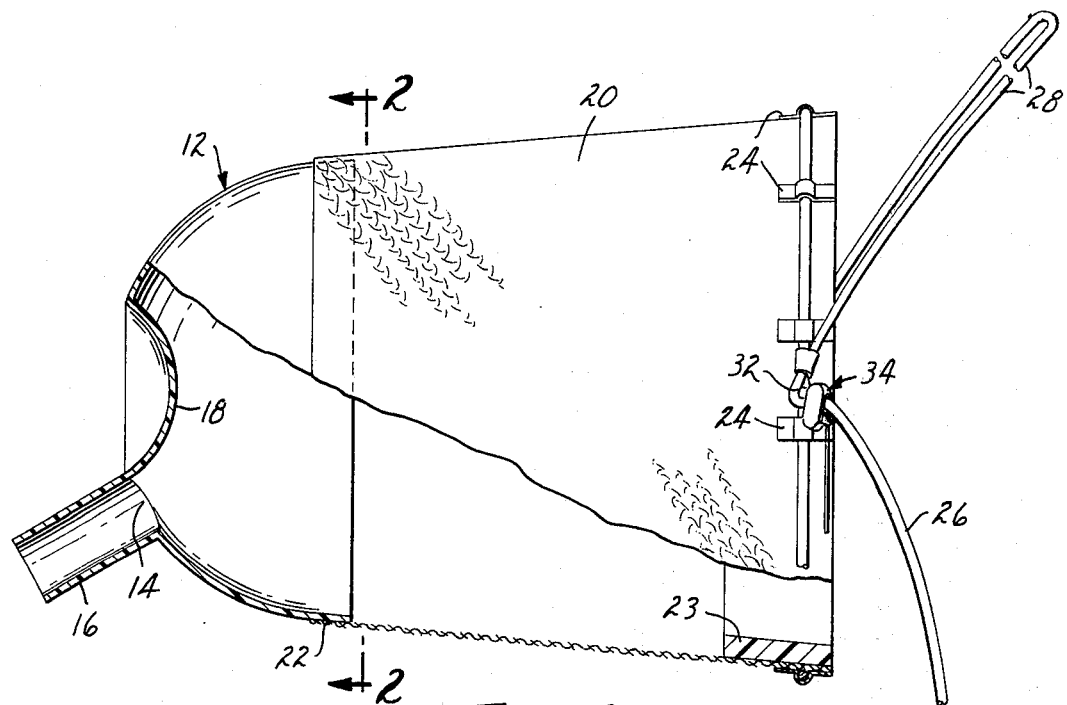
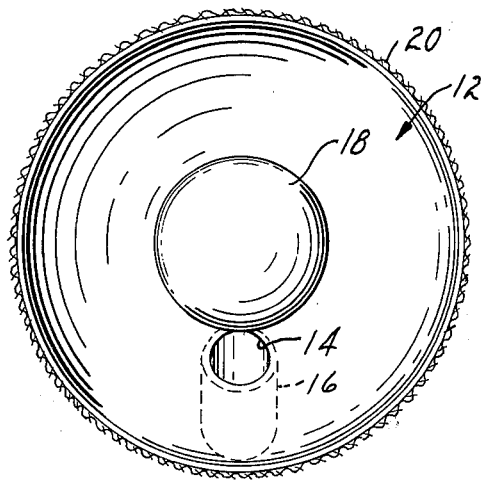
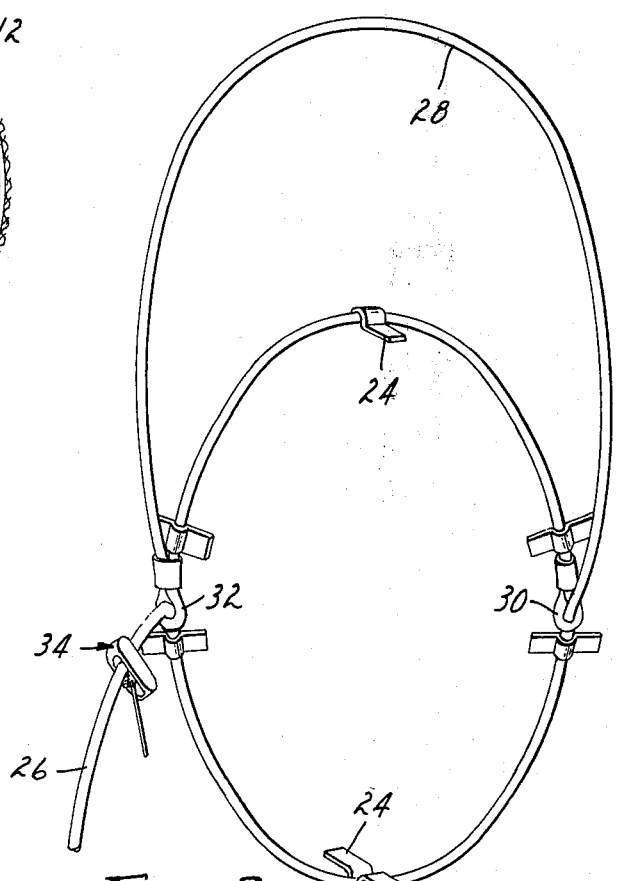

ANIMAL GAS MASK ASSEMBLY

RELATED APPLICATIONS

This application is a continuation-in-part of my copending application Ser. No. 505,618 filed Sept. 13, 1974 now abandoned.

FIELD OF THE INVENTION

This invention relates to gas masks for animals. More specifically, this invention relates to a gas mask shaped to fit over the nose and mouth of a snouted animal and which is suitable for use with a positive pressure breathing unit to administer oxygen or oxygen-enriched air to the animal.

DISCUSSION OF THE PRIOR ART

Pneumonia ranks as one of the most serious health problems in livestock. It has been estimated that this disease results in a pecuniary loss to cattle producers in this country of about one hundred million dollars each year. (Livestock Conversation, Inc., National Shipping Fever Survey, 1973). When considering the decreased weight gain of animals suffering from chronic pneumonia, the cost of medication and man hours required for treating the disease, the actual dollar loss is probably much larger.

The term "pneumonia" refers broadly to an inflammation of the lungs. The cause of the disease is usually attributed to a microorganism of some type, but various physical and chemical irritants can also contribute to the inflammation. Regardless of its etiology, the response of the lungs to the disease is well established. A fluid exudate is produced which results in congestion. The fluid exudate is gradually replaced by fibrin and the affected lung tissue solidifies into a firm, solid mass.

If the disease is controlled, the products of inflammation are broken down and removed by the body's normal repair mechanism in a process called "resolution". If resolution is delayed, irreversible changes may occur resulting in permanent loss of pulmonary function.

Pnemonia is generally treated with antibiotics to eliminate infectious organisms. In addition, certain medicaments, particularly proteolytic enzymes such as streptokinase and streptodornase, can be administered to the animal to aid in the resolution process by breaking down fibrin and other products of inflammation.

In order to maximize the effectiveness of medicaments used to treat respiratory diseases in animals, these medicaments should be delivered directly to the affected areas of the lungs by inhalation means. In severe cases of pneumonia, when breathing is particularly difficult, it may also be desirable to administer oxygen or oxygen-enriched air to the animal, alone, or in conjunction with medicaments.

Prior to the present invention there were no means available to veterinarians to efficiently administer oxygen and/or gas-suspended medicaments to an animal short of placing the animal in a body chamber containing the gas or aerosolized medicaments. Obviously, this is a highly impractical method of treating large animals.

Inhalation therapy in the treatment of respiratory diseases in humans has been practiced successfully for many years. Techniques and devices for delivering oxygen and aerosolized medicaments to the lungs of human patients have become increasingly sophisticated in recent years. Automatic breathing units have been developed which are triggered by the patient's inhalation and afford the discharging of oxygen and/or aerosolized medicament to an expanded lung.

Automatic breathing devices, generally referred to as intermittent positive pressure breathing (IPPB) units, require the use of a mouth piece device, face mask or other means held in close proximity to the patient's air passages to maintain pressure changes in the respiratory tract created during inhalation and exhalation. These pressure changes, particularly negative pressures created during inhalation, must be maintained for a sufficient length of time to be detected by the IPPB unit which is thereby triggered to discharge a stream of compressed air or oxygen to the patient.

When treating a human patient, the patient can be taught to cooperate with the breathing unit. For example, a conscious patient can be directed to place his mouth around a mouth piece. Simple face masks are also available which can be held or strapped around the nose and mouth of a human patient.

The problems associated with the use of an IPPB unit are greatly magnified when treating animals, particularly large farm animals. Animals cannot be directed to hold a mouthpiece device in their mouth. Although animal face masks were known which serve other purposes such as for warming cold air before it is inhaled or protecting the nose from attack by insects, none were adequate to serve as a gas mask for use with an IPPB unit. Consequently, prior to the present invention, inhalation therapy for the treatment of respiratory disease in large animals, utilizing automatic breathing devices, was unavailable.

The present invention effectively fulfills the above-described need by providing a gas mask for animals which can be used in conjunction with an intermittent positive pressure breathing unit to administer oxygen or oxygen-enriched air to animals suffering from respiratory diseases. The present invention provides an essentially air-tight mask shaped to fit securely over the nose and mouth of a snouted animal. The mask of the invention is capable of maintaining pressure changes in the animal's respiratory tract, created during inhalation and expiration, for a sufficient length of time to trigger an IPPB unit to discharge therapeutic gas to the animal. The present invention further provides a gas mask for animals which is adaptable to a variety of animal sizes and which results in a minimum amount of panic and/or distress to the animals. The mask is also fitted with an immobilizing cinch having a rope lock for restraining the animal during treatment.

SUMMARY OF THE INVENTION

The present invention provides a gas mask assembly for snouted animals comprising a means defining a rigid nose cap member for covering the nostrils and anterior portion of the animal's snout and having a generally circular marginal portion and an opening for the attachment of a breathing tube. The nose cap member contains abutments means for preventing the animal's nostrils from becoming occluded by the nose cap member. The abutment means comprises a member positioned symmetrical with respect to an axis through the center of the opening defined by the circular margin portion of the nose cap and intersecting the center of the end of the nose cap, and defines a surface spaced from the inner surfaces of the nose cap. This symmetrical placement of the nose abutment means allows it to contact the animal's nose in essentially the same place regardless of the orientation of the mask on the animal's snout. The mask further comprises a flexible sleeve member formed from substantially gas impermeable material and shaped to fit around the animal's snout. The sleeve member is joined to the marginal portion of the nose cap member and has an open end having immobilizing cinch means for securing and sealing the open end of the sleeve member to the animal's snout and for restraining the animal's head from movement. A rope lock on the immobilizing cinch holds the mask tight against the animal's head to maintain the mask tight against the snout. The cinch tightens against the animal's head as he struggles against the stancion to which the cinch is secured.

When the mask is tightly fitted over the animal's snout, the mask can be connected by a breathing tube to an IPPB unit. The breathing tube contains an exhalation valve which allows air above a predetermined pressure to escape. The exhalation valve is attached by a triggering line to the IPPB unit. When the animal inhales, a negative pressure is created in the mask and breathing tube which is detected by the IPPB unit via the triggering line. The IPPB unit then discharges gas from a source of compressed air or oxygen into the breathing tube. When the pressure in the animal's lungs builds up to a predetermined pressure, the IPPB unit shuts off and the animal exhales. When the animal takes his next breath, the IPPB unit is again triggered and the operation continues until the desired treatment has been given.

The gas mask of the present invention is an essential element in a system for injecting dry medicaments in a gaseous suspension into the trachea of an animal utilizing an IPPB unit. This system is described in U.S. Pat. No. 3,915,165, incorporated herein by reference. The mask is especially suited for use in the system described therein because of the immobilizing cinch which restrains the animal during tracheal puncture and the subsequent treatment period. The mask of the present invention may also be used for giving oxygen therapy or for administering other gases such as anesthetic gases to animals.

DESCRIPTION OF THE DRAWINGS

Understanding of the invention will be facilitated by reference to the accompanying drawings in which like numbers refer to like parts in several views and wherein:

FIG. 1 is a side view of the mask, partially in section, and showing the rope lock of the immobilizing cinch tightened against the mask;

FIG. 2 is a sectional view taken along line 2—2 of FIG. 1;

FIG. 3 is a perspective view of the immobilizing cinch;

In FIG. 1, a nose cap 12 forms the front rigid section of the mask and covers the nostrils and anterior portion of the animal's snout. Nose cap 12 has a generally circular marginal portion. The nose cap may be formed from any lightweight material, and is preferably made by molding from a high impact plastic such as a polyolefin or ABS (acrylonitrile-butadiene-styrene). The function of the nose cap is to prevent the end of the mask from collapsing around the animal's nostrils. Nose cap 12 contains an opening 14 and attaching collar 16 for the attachment of a breathing tube to the mask.

Nose cap 12 contains an abutment means for preventing the animal's nostrils from being occluded by the nose cap if the mask is drawn too tightly over the snout of the animal. In FIG. 1, this abutment means is illustrated as a rounded protrusion 18 placed or molded in a central interior position at the end of the nose cap 12. Protrusion 18 is positioned symmetrical with respect to an axis through the center of the opening defined by the circular marginal portion of nose cap 12 and intersecting the center of the end of nose cap 12, and defines a surface spaced from the inner surfaces thereof. The tip of protrusion 18 contacts the area of the animal's snout between the nostrils. The animal's nostrils, being lateral to the point of contact of the protrusion 18 with the center of the animal's nose, are free from occlusion.

Figure 4:
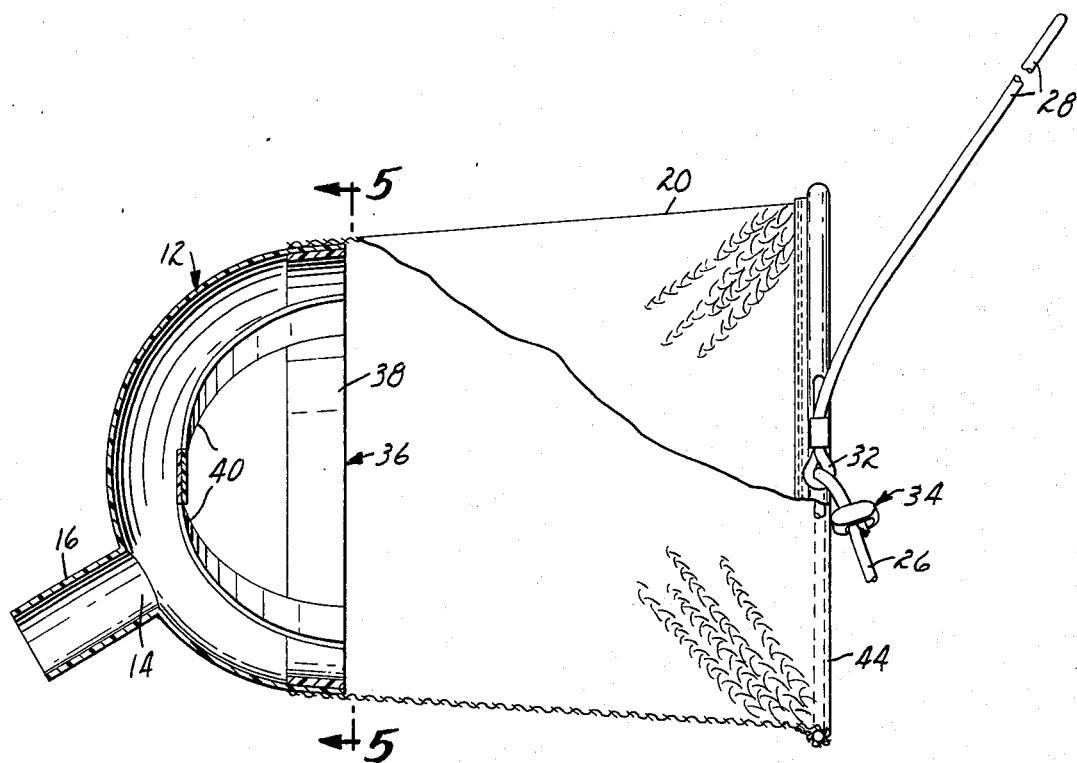
FIG. 4 is a side view of the mask partially in section illustrating an alternative embodiment of the mask of the present invention.

The marginal portion of nose cap 12 is joined to one end of a flexible sleeve member 20 along a seam 22 by an adhesive such as a tent fabric seam sealer adhesive (available from Eureka Tent and Awning, Binghamton, New York, USA). Sleeve member 20 can be made from any gas impermeable material which is flexible enough to allow for adjustment when fitting a variety of snout sizes. It has been found that rubberized or coated nylon tent fabric works well for this purpose as well as polyethylene. The length of sleeve member 20 will be determined by the length of the animal's snout. When fitted onto the animal's snout, it should be positioned so as not to cover the animal's eyes.

The opposite end of sleeve member 20 from the end sealed to the nose cap 12 (open end) is preferably fitted on its inner surface with a gasket 23 of a compressible material such as closed cell foam. Gasket 23 aids in forming a substantially air-tight seal when the mask is tightened around the animal's snout. An inflatable bladder may also be provided in place of the gasket, which bladder could be inflated by the air discharged into the mask, and in its inflated state, prevent air from escaping from the mask.

In the embodiment of FIG. 1, the open end of sleeve member 20 contains a plurality of belt loops 24 which are spaced apart from one another and sealed, by heat or adhesive, to the exterior surface. Rope 26 is supported by belt loops 24 and forms the immobilizing cinch illustrated more completely in FIG. 3. As rope 26 is tightened in the manner described hereinbelow the open end of sleeve member 20 is secured and sealed around the animal's snout to prevent gas from entering or escaping from the marginal portion of the mask.

FIG. 2 illustrates a cross section of the mask taken alone line 2—2 of FIG. 1 wherein rounded protrusion 18 is shown in the center of nose cap 12. Opening 14 and attaching collar 16 provide means for attaching a breathing tube.

FIG. 3 illustrates the immobilizing cinch wherein a rope 26 has a fixed rope loop 30 at one end and a fixed rope loop 32 spaced a predetermined distance from loop 30. When the immobilizing cinch is attached to the open end of sleeve member 20, by passing through belt loops 24, rope loops 30 and 32 are on opposite sides of sleeve member 20. Rope 26 extends from rope loop 32 to form a band portion 28 which is placed behind the animal's ears. After forming the band 28, rope 26 passes through loop 30 and about the under portion of the mask, where it is held by belt loops 24, and through the rope loop 32. The rope 26 then passes through a rope lock 34 which prevents the rope from loosening after it is tightened. When the mask is in place on the animal, the free end of rope 26 is tightened to secure the open end of sleeve member 20 around the animal's snout and tightens the band portion of rope 26 behind the animal's ears. The rope is locked by rope lock 34 and the free end of rope 26 is tied to a stanchion or other support. If the animal struggles in a direction away from the stanchion the immobilizing cinch will be drawn tighter around the animal and make further movement more uncomfortable.

Figure 5:
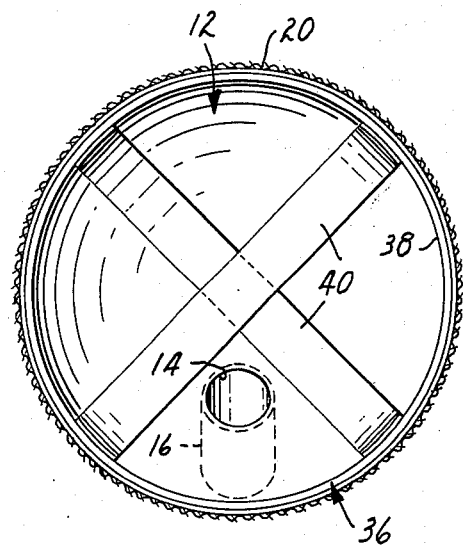
FIG. 5 is a sectional view taken along line 5—5 of FIG. 4.

FIG. 4 illustrates an alternative embodiment of the mask of the invention. In this embodiment, a nose frame 36 is fitted snugly inside the nose cap 12. The frame 36 comprises a circular band 38 and a pair of arcuate bands 40 secured tightly thereto and intersecting to form a barrier, as shown in the cross-sectional view of FIG. 5. The cage formed by the bands 40 allows air to flow freely to the animal's nostrils through the large openings between the bands. More intersecting bands of smaller size could be used if desired.

Nose frame 36 may be formed from any rigid, lightweight material such as molded plastic, aluminum strappings or wire. The design of the nose frame may vary greatly so long as its solid areas are not large enough to occlude the animal's nostrils and it contains openings in its structure for the free flow of air therethrough.

FIG. 4 illustrates the preferred means of attaching the immobilizing cinch to the open end of sleeve member 20. In this embodiment the open end of sleeve member 20 is folded back on itself and stitched or sealed to form a casing 44 to receive rope 26. Casing 44 contains an opening at the location of rope loop 30 and a second opening opposite the first opening to expose rope loop 32. When the free end of rope 26 is tightened, the casing 44 is drawn together and seals the open end of sleeve member 20 against the animal's snout.

Figures 6, 7:
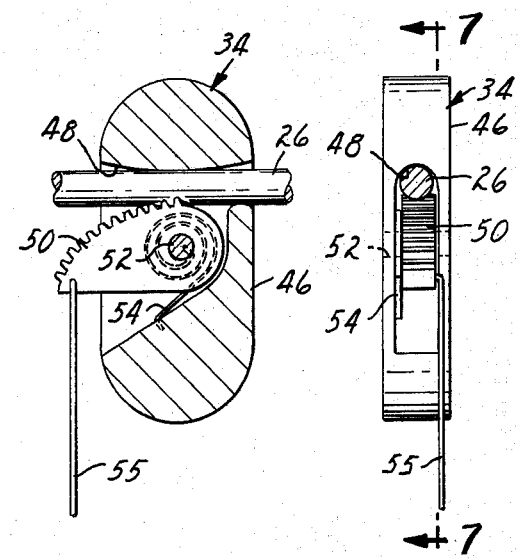
FIG. 6 is an end view of the rope lock.
FIG. 7 is a sectional view taken along line 7—7 of FIG. 6.

FIGS. 6 and 7 illustrate rope lock 34 which has a housing 46 with a rope passage 48 through which rope 26 passes. Housing 46 contains a recess holding a locking wedge 50 which is pivoted about pin 52 and bears teeth on the surface adjacent to rope 26. Locking wedge 50 is biased against the rope by torsion spring 54, also pivoted about pin 52. Release wire 55 is secured to locking wedge 50 to move it against the bias of torsion spring 54 and release the rope. The rope lock prevents the rope from loosening after the mask has been tightly secured to the animal. If the animal struggles, the locking wedge is forced tighter against the rope thus making further struggle increasingly uncomfortable.

The mask assembly of the present invention is especially designed for livestock such as cattle, horses, swine, etc. Because a nose abutment means is provided which prevents the nostrils of the animal from becoming occluded by the nose cap, a universal mask may be made to fit all adult animals of these species. Modifications in the size of the mask may be made, however, to fit small snouted animals such as dogs, cats or sheep.

The mask of the present invention is used with a breathing tube containing an exhalation valve to enable the animal to exhale. The breathing tube may be attached to any source of compressed gas desired, depending upon the type of treatment the animal is receiving. An intermittent positive pressure breathing unit such as the Monaghan "M520 I.P.P.B." unit, available from Monaghan, 4100 East Dry creek Road, Littleton, Colorado, USA, 80122, is preferably used to regulate the flow of gas to the mask.

What is claimed is:

1. A gas mask assembly for snouted animals comprising:
   a. means defining a rigid nose cap member for covering the nostirls and anterior portion of the animal's snout and having a generally circular marginal portion and means defining an opening in said nose cap member for the attachment of a breathing tube;
   b. abutment means in said nose cap member for preventing the animal's nostrils from becoming occluded by said nose cap member, said abutment means comprising a member positioned symmetrical with respect to an axis through the center of the opening defined by said circular marginal portion of said nose cap and intersecting the center of the end of said nose cap and defining a surface spaced from the inner surfaces thereof;
   c. a flexible sleeve member formed from substantially gas-impermeable material and shaped to fit around the animal's snout, said sleeve member being joined to the marginal portion of said nose cap member; and
   d. immobilizing cinch means secured to the open end of said sleeve member and including a rope lock for securing and sealing said sleeve member to the animal's snout and for restraining the animal's head and allowing the cinch to tighten as the animal struggles against said immobilizing cinch means.

2. Gas mask assembly according to claim 1 wherein the nose abutment means comprises at least one protrusion in the interior center of the nose cap member, the end of said protrusion being positioned in the mask to make contact with the area of the animal's snout between the nostrils.

3. Gas mask assembly according to claim 1 wherein the nose abutment means comprises a nose frame placed in the nose cap member and spaced from the end and having a plurality of intersecting members, each of said members being narrower than the width of the animal's nostril.

4. Gas mask assembly according to claim 1 having a gasket of compressible material around the interior surface of the open end of said sleeve member.

* * * * *